United States Patent
Kyung et al.

(10) Patent No.: US 9,290,508 B2
(45) Date of Patent: Mar. 22, 2016

(54) METHOD FOR PREPARING HIGH PURITY ANHYDROSUGAR ALCOHOLS BY THIN FILM DISTILLATION

(71) Applicant: SAMYANG GENEX CORPORATION, Seoul (KR)

(72) Inventors: Do Hyun Kyung, Daejeon (KR); Young Jae Jung, Seoul (KR); Jin Kyung Kim, Daejeon (KR); Hoon Ryu, Daejeon (KR)

(73) Assignee: SAMYANG GENEX CORPORATION, Seoul (KR)

( * ) Notice: Subject to any disclaimer, the term of this patent is extended or adjusted under 35 U.S.C. 154(b) by 0 days.

(21) Appl. No.: 14/399,031

(22) PCT Filed: May 9, 2013

(86) PCT No.: PCT/KR2013/004077
§ 371 (c)(1),
(2) Date: Nov. 5, 2014

(87) PCT Pub. No.: WO2013/169029
PCT Pub. Date: Nov. 14, 2013

(65) Prior Publication Data
US 2015/0112088 A1  Apr. 23, 2015

(30) Foreign Application Priority Data
May 11, 2012 (KR) .......................... 10-2012-0050316

(51) Int. Cl.
| | | |
|---|---|---|
| C07D 493/04 | (2006.01) |
| B01D 1/22 | (2006.01) |
| B01D 3/00 | (2006.01) |
| C07C 29/80 | (2006.01) |
| B01D 1/06 | (2006.01) |
| B01D 5/00 | (2006.01) |

(52) U.S. Cl.
CPC .............. *C07D 493/04* (2013.01); *B01D 1/065* (2013.01); *B01D 1/22* (2013.01); *B01D 3/00* (2013.01); *B01D 5/006* (2013.01); *B01D 5/0063* (2013.01); *C07C 29/80* (2013.01)

(58) Field of Classification Search
USPC .......................................................... 549/464
See application file for complete search history.

(56) References Cited

U.S. PATENT DOCUMENTS

| | | |
|---|---|---|
| 3,454,603 A | 7/1969 | Hartmann et al. |
| 4,506,086 A | 3/1985 | Salzburg et al. |
| 4,564,692 A | 1/1986 | Feldmann et al. |
| 5,558,893 A | 9/1996 | Muraldihara |
| 7,439,352 B2 | 10/2008 | Moore et al. |
| 2004/0110969 A1 | 6/2004 | Fleche et al. |
| 2005/0020807 A1 | 1/2005 | Boon et al. |

FOREIGN PATENT DOCUMENTS

| | | |
|---|---|---|
| EP | 0 716 867 A1 | 6/1996 |
| WO | WO 00/14081 A1 | 3/2000 |

OTHER PUBLICATIONS

Fleche et al., "Isosorbide (Preparation, Properties and Chemistry)," Starch/Starke, 1986, vol. 38, No. 1, pp. 26-30.
International Search Report issued in PCT/KR2013/004077, mailed on Aug. 29, 2013.
Pi, P.H. et al, "Heat Transfer and Evaporating Performance of the New-Type Inner-Condensing Thin-Film Evaporator," Journal of South China University of Technology, 2002, vol. 30, No. 8, pp. 69-72.

*Primary Examiner* — Kristin Vajda
(74) *Attorney, Agent, or Firm* — Birch, Stewart, Kolasch & Birch, LLP

(57) ABSTRACT

The present invention relates to a method for preparing high purity anhydrosugar alcohols using hydrogenated sugar, and more specifically, to a method for preparing high purity anhydrosugar alcohols (particularly, isosorbide, isomannide, isoidide, and the like) with a purity of 97.5% or higher (more preferably, 98.5% or higher) and a pH of a distillate of 3.7 or higher (more preferably, 4.0 or higher) in a distillation yield of 87% or higher (more preferably, 90% or higher) by adding an acid to hexitol so as to convert the same into anhydrosugar alcohols, and single-stage distilling the converted product by using an internal condenser type thin film evaporator.

11 Claims, 1 Drawing Sheet

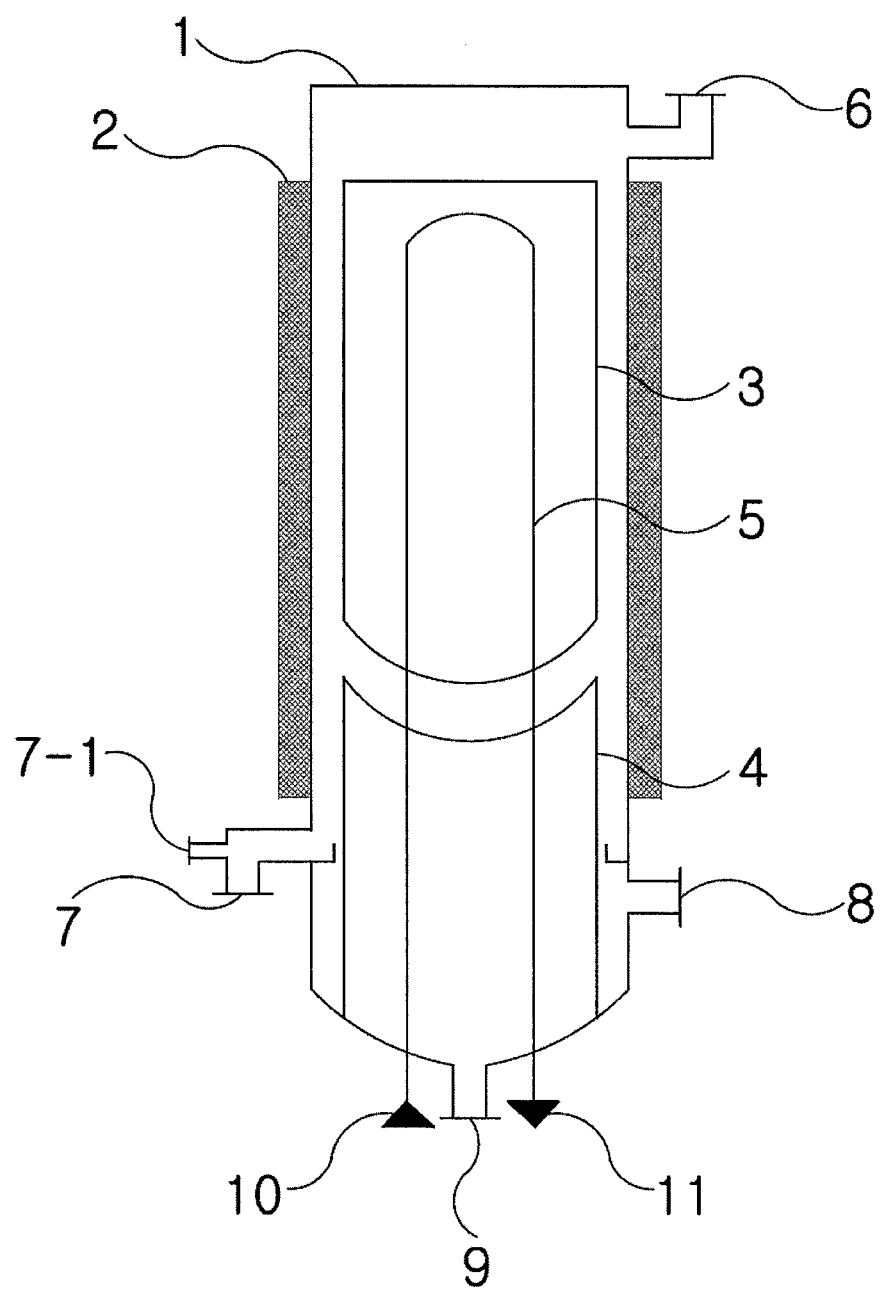

METHOD FOR PREPARING HIGH PURITY ANHYDROSUGAR ALCOHOLS BY THIN FILM DISTILLATION

TECHNICAL FIELD

The present invention relates to a technology for producing anhydrosugar alcohol by using hydrogenated sugar as raw material, and more specifically a technology capable of producing highly pure anhydrosugar alcohol (particularly, isosorbide, isomannide, isoidide, etc.) having a purity of 97.5% or higher (more preferably, 98.5% or higher) and a distillate pH of 3.7 or higher (more preferably, pH 4.0 or higher) with a distillation yield of 87% or higher (more preferably, 90% or higher) by the conversion of hexitol to anhydrosugar alcohol by addition of an acid thereto, and the single-step distillation of the resulting liquid of the conversion reaction by using an internal condenser type, thin-film evaporator.

BACKGROUND ART

Starch is a representative biomass and can be a major raw material of the environmentally friendly, green industry which will be developed in the future. In particular, starch is a material which can be used in the plastics industry using petroleum resources mainly and thus can actively respond to the carbon dioxide problem now seen as the main cause of global warming. However, in case of using starch as itself in the plastics industry, it is difficult to overcome the limitation in starch's properties.

Anhydrosugar alcohol can be produced by using hexitol derived from starch and has wide applicability in the fields of drug industry, chemical industry, etc. Anhydrosugar alcohol derivatives are useful for heart and blood vessel diseases and can be used in medicaments such as patch adhesive, mouthwash, etc., and also can be applied in cosmetic compositions. In addition, if polyester, polyurethane, epoxy resin, etc. are prepared by using anhydrosugar alcohol, it is possible to provide various properties to the resin. Anhydrosugar alcohol can also be used as a raw material of plasticizer, organic solvent, etc. As such, if anhydrosugar alcohol is used in the field of resin production, heat-resistant PET, polyester fiber, high-strength sheet, film, polyurethane, etc. can be produced in a more environmentally friendly manner.

Technologies using hexitol to produce anhydrosugar alcohol have been introduced in many patents, and the production methods can be classified largely into the batch process (Starch/Starke, vol. 38, pp. 26-30, and U.S. Pat. Nos. 3,454,603, 4,564,692, 4,506,086, etc.) and the continuous process (WO 00/14081).

In a general batch process, hexitol is dehydrated by using an acid catalyst (e.g., inorganic acid, cationic resin, zeolite, etc.) in a batch reactor under reduced pressure conditions, and the reaction product is subjected to one or a combination of two or more purification processes such as distillation, recrystallization (e.g., using acetone, alcohol, ethyl acetate, water, etc.), melt-crystallization, active carbon purification, ion purification, etc., to produce anhydrosugar alcohol. On the other hand, in a continuous process—for example, as disclosed in WO 00/14081—anhydrosugar alcohol generated during the reaction is continuously extracted and isolated, and the organic solvent is recirculated, to produce anhydrosugar alcohol continuously.

In order to produce anhydrosugar alcohol economically, it is essential to employ a technology of distilling anhydrosugar alcohol from the resulting liquid of conversion reaction within a short time with high yield and high purity.

As a distillation technology of distilling the conversion liquid after dehydration reaction, batch distillation or simple distillation—wherein anhydrosugar alcohol is simply distilled under reduced pressure directly after the conversion reaction in the reactor—is known.

By the batch distillation or simple distillation, however, commercial-scale economical production is difficult since the distillation time is long. In addition, if the resulting liquid of a conversion reaction is distilled at a low temperature (e.g., 170° C. or lower), the distillation time increases, and if distilled at a relatively high temperature (e.g., 170° C. or higher), the distillation time decreases but the anhydrosugar alcohol is thermally decomposed at 170° C. or higher, and byproducts such as formic acid, furfural, etc. are generated, by which the purity of the product and the pH of the distillate are lowered. That is, as compared with the wiped-film evaporation explained below, since the batch distillation or simple distillation requires relatively longer retention time of distillate and higher distillation temperature, thermal decomposition of alcohol is induced, generating the problem of lowering purity and yield of the distillate. To prevent such a thermal decomposition, use of an additive is required.

In order to overcome the deficiencies of batch distillation or simple distillation in distilling anhydrosugar alcohol from the resulting liquid of a conversion reaction, U.S. Pat. No. 7,439,352 suggested a technology of distilling anhydrosugar alcohol by wiped-film evaporation using an external condenser. In the wiped-film evaporation technology disclosed in this US patent, the condenser is operated outside of the distillator. In this type, however, the maximum vacuum circumstance that can be formed in the distillator technically is 1 mmHg; under such a vacuum degree the distillation temperature should be 170° C. or higher in order to conduct the distillation effectively. However, as stated earlier the anhydrosugar alcohol such as isosorbide is thermally decomposed at a distillation temperature of 170° C. or higher, and thereby the distillation yield and distillation purity are lowered. Accordingly, in the above US patent, the purity of the single-step distillation product is 97.1% or the like and the distillation yield is 80% or the like. However, such levels of purity and yield are still not suitable for a commercial-scale mass-production process.

Therefore, a technology of producing anhydrosugar alcohol, which can provide high purity and high yield suitable for a mass-production process on a commercial scale even by a single-step treatment of the resulting liquid of a conversion reaction, is required.

CONTENTS OF THE INVENTION

Problems to be Solved

To resolve the problems of the prior arts as explained above, the present invention has an object of providing a method which can produce anhydrosugar alcohol with high purity and high yield suitable for a mass production process on a commercial scale by only a single-step distillation treatment after converting hydrogenated sugar to anhydrosugar alcohol.

Technical Means

To achieve the above-stated object, the present invention provides a method for producing anhydrosugar alcohol comprising the steps of converting hydrogenated sugar to anhydrosugar alcohol by dehydration reaction, and distilling the resulting liquid of the converting step, wherein the distilling step is conducted in an internal condenser type, thin-film evaporator comprising an internal condenser, an input line for raw material, an output line for distillation residue, a vacuum line and an output line for distillate.

According to a preferred aspect of the present invention, in the above method for producing anhydrosugar alcohol, when the distilling step is conducted, the inside of the evaporator is depressurized by pressure reduction through the vacuum line and additionally through the output line for distillation residue.

The other aspect of the present invention provides an internal condenser type, thin-film evaporator comprising an internal condenser, an input line for raw material, an output line for distillation residue, a vacuum line and an output line for distillate, wherein the output line for distillation residue has a branch line for vacuum formation.

Effect of the Invention

According to the present invention, it is possible to produce anhydrosugar alcohol with high purity (purity of 97.5% or higher, more preferably 98.5% or higher; distillate pH of 3.7 or higher, more preferably 4.0 or higher) and high yield (distillation yield of 87% or higher, more preferably 90% or higher) suitable for a mass-production process on a commercial scale, by only a single-step distillation treatment after converting hydrogenated sugar to anhydrosugar alcohol.

BRIEF EXPLANATION OF THE DRAWINGS

FIG. 1 schematically represents a structure of a preferable embodiment of an internal condenser type, thin-film evaporator which can be used in the method for producing anhydrosugar alcohol of the present invention.

CONCRETE EXPLANATION TO CARRY OUT THE INVENTION

The present invention is explained in more detail below.

The method for producing anhydrosugar alcohol of the present invention comprises a step of converting hydrogenated sugar to anhydrosugar alcohol by dehydration reaction.

Hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar (or sugar alcohol) in one or more steps by any method.

In the present invention, hexitol is preferably used as the hydrogenated sugar, and more preferably, the hydrogenated sugar for use is selected from sorbitol, mannitol, iditol and mixtures thereof.

Accordingly, in the present invention, dianhydrohexitol—which is the dehydrated product of hexitol—is preferably obtained as the anhydrosugar alcohol, and more preferably, the obtained anhydrosugar alcohol is selected from isosorbide (1,4-3,6-dianhydrosorbitol), isomannide (1,4-3,6-dianhydromannitol), isoidide (1,4-3,6-dianhydro iditol) and mixtures thereof. Among them, isosorbide is particularly useful for industrial and medicinal application.

The hydrogenated sugar is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol, and more preferably, acid mixture of a first acid and a second acid can be used. As for the acid catalyst, in the case of a single acid catalyst, sulfuric acid, hydrochloric acid, phosphoric acid, etc. can be used; and in the case of an acid mixture, sulfuric acid can be used as the first acid, and one or more sulfur-containing acids or salts thereof selected from the group consisting of p-toluenesulfonic acid, methanesulfonic acid, ethanesulfonic acid, benzenesulfonic acid, naphthalenesulfonic acid and aluminum sulfate can be used as the second acid. The acid catalyst is preferably used in an amount of from 0.5 to 10 parts by weight per 100 parts by weight of the hydrogenated sugar (e.g., hexitol). If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

According to an embodiment of the present invention, the step of converting hydrogenated sugar to anhydrosugar alcohol may be conducted in the presence of an acid catalyst as explained above, at a temperature of from 100 to 190° C. under a pressure of 20 mmHg or less for 1 hour to 10 hours.

In the case of using an acid catalyst during the dehydration reaction of hydrogenated sugar, it is preferable to neutralize the reaction product liquid. The neutralization may be conducted by, after the dehydration reaction, cooling the reaction product liquid (e.g., to 100° C. or lower) and adding thereto conventional alkali such as sodium hydroxide. The neutralized reaction product liquid preferably has a pH of 6 to 8.

According to a preferable embodiment of the method for producing anhydrosugar alcohol of the present invention, the resulting liquid of the step of converting hydrogenated sugar to anhydrosugar alcohol may be pre-treated before being fed to the distilling step. The purpose of the pre-treatment is to remove moisture and low-boiling-point substance(s) remaining in the resulting liquid of the converting step, and may be conducted conventionally at a temperature of from 90° C. to 110° C. under a pressure of 10 mmHg to 100 mmHg for 1 hour or longer (e.g., 1 to 4 hours), but it is not limited thereto.

The resulting liquid of the step of converting hydrogenated sugar to anhydrosugar alcohol (preferably, the pre-treated resulting liquid as explained above) is distilled in an internal condenser type, thin-film evaporator.

A structure of a preferable embodiment of an internal condenser type, thin-film evaporator which can be used in the distilling step in the method for producing anhydrosugar alcohol of the present invention is schematically represented in FIG. 1. The internal condenser type, thin-film evaporator 1 according to FIG. 1 comprises internal condenser 5, input line for raw material 6, output line for distillation residue 7, branch line for vacuum formation 7-1, vacuum line 8 and output line for distillate 9, and further comprises heating jacket 2 for heating, wiper 3, condenser guard 4 and cooler input/output lines 10 and 11, respectively. The internal condenser type, thin-film evaporator which can be used in the present invention is not limited to that of the structure shown in FIG. 1, and if necessary, it may further comprise additional components other than the above-explained ones, and the forms thereof may be various.

The distilling step can be conducted effectively under a temperature condition of preferably from 100° C. to 200° C., more preferably from 100° C. to 170° C., and still more preferably from 110° C. to 160° C. If the distillation temperature is lower than 100° C., the distillation of anhydrosugar alcohol may not be conducted effectively. If the distillation temperature is higher than 200° C., anhydrosugar alcohol may be carbonized or polymer material may be generated, and the color will become dark due to the formation of coloring substance, rendering decolorization difficult. Furthermore, anhydrosugar alcohol is thermally decomposed at high temperature and thus byproducts such as formic acid, furfural, etc. are generated, and they lower the purity and pH of the resulting liquid of distillation, which is not industrially preferable.

Under the above preferable temperature condition, the pressure condition (inside the reactor) of the distilling step is preferably 10 mmHg or less (e.g., 0.0001 to 10 mmHg), more preferably 5 mmHg or less (e.g., 0.001 to 5 mmHg), and still more preferably 1 mmHg or less (e.g., 0.01 to 1 mmHg, more concretely 0.1 to 0.7 mmHg). If the distillation pressure is greater than 10 mmHg, the distillation temperature should be elevated in order to distill anhydrosugar alcohol and in such a case, the aforesaid problems may be generated. On the other hand, excessively low distillation pressure is not preferable since an extra cost would be necessitated for a high-vacuum device to lower the distillation pressure.

According to a preferable embodiment of the present invention, when the distilling step is conducted, in addition to the depressurization of the inside of the evaporator through the vacuum line it is possible to further depressurize it through the output line for distillation residue.

Conventional wiped-film evaporation using an external condenser could not provide a high-vacuum condition of 1 mmHg or less and thus had a disadvantage that the distillation temperature should be increased. However, the present invention using an internal condenser type, thin-film evaporator can lower the pressure in the evaporator more effectively, and the pressure in the evaporator can be lowered more preferably to 1 mmHg or less by additional pressure reduction through the output line for distillation residue, whereby the distillation temperature can be further lowered (e.g., 170° C. or lower to 100° C.) and thus the thermal decomposition of the target product anhydrosugar alcohol can be prevented, and the purity and yield of the distillate can be further improved. In addition, more preferably the flowability of the distillation residue stream can be improved by additional pressure reduction through the output line for distillation residue, and the problem of condenser contamination due to the distillation residue can be resolved thereby.

In particular, given the lowering of the distillation temperature, the effect of improving pH of the distillate can be obtained. If isosorbide—which is an anhydrosugar alcohol— is thermally decomposed, byproducts such as formic acid, furfural, etc. are generated, and these byproducts lower pH of the distillate, and as pH of the distillate is lowered, the stability of the prepared isosorbide becomes worse. Thus, it is necessary to maintain pH of the final distillate at 6.0 or higher through ion purification. However, if the byproducts are generated in large amount due to high distillation temperature, the subsequent ion purification is overloaded, which is problematical. According to the present invention, since the pressure in the evaporator can be lowered effectively and thus the distillation temperature can be lowered further and generation of the thermal decomposition byproducts can be prevented, pH of the distillation product liquid can be increased and the load applied to the ion purification step after the distillation step can be reduced, by which anhydrosugar alcohol can be produced more economically. According to a preferable embodiment of the present invention, the distillation temperature can be lowered to 145° C. and as a result, anhydrosugar alcohol with purity of 98.5% or higher (e.g., 98.5 to 100%) and distillate pH of 4.0 or higher (e.g., 4.0 to 7.0) can be obtained in distillation yield of 90% or higher (e.g., 90 to 100%).

In a preferable embodiment of the present invention, there is no special limitation in the method of additionally depressurizing the inside of the evaporator through the output line for distillation residue. For example, a vacuum pump connected to the vacuum line can also be connected to the branch line for vacuum formation of the output line for distillation residue, by which the same degree of vacuum can be applied to the output line for distillation residue and the vacuum line. Alternatively, a separate vacuum pump can be connected to the branch line for vacuum formation of the output line for distillation residue, by which an independent degree of vacuum from the vacuum line can be applied to the output line for distillation residue.

With reference to FIG. 1, an embodiment of conducting distillation by connecting the same vacuum pump to the vacuum line and the branch line for vacuum formation of the output line for distillation residue is explained below.

In conventional wiped-film evaporation, a vacuum pump (not shown) is connected to the vacuum line 8 only, and accordingly the relative pressure relationship inside the evaporator is: [vacuum line 8<inside of condenser guard 4<outside of condenser guard 4=output line for distillation residue 7]. In this, because the pressure at the output line for distillation residue 7 is greater than those of the in- and outsides of condenser guard 4, the flow of distillation residue is disturbed. To the contrary, if the same vacuum pump is connected to the vacuum line and the branch line for vacuum formation of the output line for distillation residue 7-1 and operated according to the preferable embodiment of the present invention, the relative pressure relationship inside the evaporator becomes: [vacuum line 8=output line for distillation residue 7<outside of condenser guard 4=inside of condenser guard 4]. Thus, the high-vacuum state can be maintained more effectively and the flow of distillation residue can also be improved effectively. In the above, "=" means the same or a similar level of pressure.

The method for producing anhydrosugar alcohol of the present invention may further comprise, after the distilling step, a step of conducting post-treatment for the anhydrosugar alcohol resulting from the distillation, wherein the post-treatment is selected from adsorbent treatment, ion purification, and a combination thereof.

The adsorbent treatment is for decolorization and may be conducted by using a conventional adsorbent such as active carbon according to the conventional method of adsorbent treatment. As the active carbon, one or more selected from active carbon groups obtained by activating plant sources such as wooden material, palm, etc. or mineral sources such as brown coal, bituminous coal, soft coal, anthracite coal, etc. may be used.

The purpose of the ion purification is to remove ions that may exist in the anhydrosugar alcohol, and can be conducted 1 time or more using one or more ion exchange resins selected from strong cationic, weak cationic, strong anionic and weak anionic ion exchange resin groups according to the ion types that may exist.

According to a preferable embodiment of the present invention, after converting hexitol as the hydrogenated sugar to anhydrosugar alcohol, even the single-step distillation treatment can provide highly pure anhydrosugar alcohol with purity of 98.5% or higher and distillate pH of 4.0 or higher in distillation yield of 90% or higher, and subsequently conducting the decolorization by adsorbent and ion purification procedure can provide white isosorbide.

The distillation method according to a preferable embodiment of the present invention is preferably used in distilling anhydrosugar alcohol, and can also be applied to distillation of other materials. From this viewpoint, another aspect of the present invention provides a method for distilling liquid material by using an internal condenser type, thin-film evaporator comprising an internal condenser, an input line for raw material, an output line for distillation residue, a vacuum line and an output line for distillate, wherein when the distillation is conducted, the inside of the evaporator is depressurized by pressure reduction through the vacuum line and additionally through the output line for distillation residue.

Furthermore, another aspect of the present invention provides an internal condenser type, thin-film evaporator comprising an internal condenser, an input line for raw material, an output line for distillation residue, a vacuum line and an output line for distillate, wherein the output line for distillation residue has a branch line for vacuum formation. The concrete embodiment of the internal condenser type, thin-film evaporator of the present invention and example used thereof are explained above, but it is not limited thereto.

The present invention is explained in more detail through the following Examples and Comparative Examples. However, the Examples are intended to facilitate understanding of the present invention only, and the scope of the present invention is not limited thereby.

EXAMPLES

Example 1

10,000 g of sorbitol powder (D-sorbitol, Samyang Genex Inc.) was fed into a batch reactor equipped with an agitator and melted by heating to 110° C. 100 g of sulfuric acid (Duksan Chemical) and 42 g of methanesulfonic acid were added thereto, and the reactor was heated to about 140° C. Dehydration reaction was conducted under a reduced pressure condition of about 30 mmHg to convert sorbitol to anhydrosugar alcohol. After the dehydration reaction was completed, the reaction mixture was cooled to 110° C., and about 300 g of 50% sodium hydroxide solution (Samjeon Pure Chemical) was added thereto to neutralize the resulting reaction liquid. The resulting neutralized liquid was set to be at 100° C. and then concentrated under a reduced pressure condition of 40 mmHg or less for 1 hour or longer to remove the moisture and low-boiling-point substance present in the resulting liquid. After the neutralization and moisture removal were completed, the resulting liquid was analyzed. The results were 74% of conversion rate of sorbitol, 1% by weight of sorbitan and sorbitan isomer content in the resulting liquid, and 15% of other polymer content.

The resulting liquid after the neutralization and moisture removal was distilled by using an internal condenser type, thin-film evaporator under conditions of 170° C. of distillation temperature and 0.70 mmHg of evaporator inside pressure. At that time, the distillation was conducted by connecting a vacuum pump to the vacuum line, and additionally to the branch line for vacuum formation of the output line for distillation residue, by which continuous distillation was possible even under 1.40 mmHg or less of evaporator inside pressure. The obtained distillate showed 97.5% of isosorbide purity, pH 3.70, yellow color and 92.0% of distillation yield, and the distillation time was 4 hours or less.

Gas chromatography (GC, HP) was used to analyze the resulting product.

Conversion rate=[moles of produced anhydrosugar alcohol/moles of fed hexitol(sorbitol)]*100

Distillation yield=[wt % of anhydrosugar alcohol in distillate/wt % of anhydrosugar alcohol in resulting liquid of conversion]*100

Example 2

The resulting liquid of conversion obtained after the neutralization and moisture removal in Example 1 was distilled by thin-film evaporation. Other than the fact that the distillation temperature was set to 160° C. and the evaporator inside pressure was set to 0.45 mmHg, the distillation was conducted in the same manner using the same thin-film evaporator as Example 1. The obtained distillate showed 98.5% of isosorbide purity, pH 4.00, yellow color and 92.0% of distillation yield, and the distillation time was 4 hours or less.

Example 3

The resulting liquid of conversion obtained after the neutralization and moisture removal in Example 1 was distilled by thin-film evaporation. Other than the fact that the distillation temperature was set to 150° C. and the evaporator inside pressure was set to 0.14 mmHg, the distillation was conducted in the same manner using the same thin-film evaporator as Example 1. The obtained distillate showed 98.5% of isosorbide purity, pH 4.50, yellow color and 91.6% of distillation yield, and the distillation time was 4 hours or less.

Example 4

The resulting liquid of conversion obtained after the neutralization and moisture removal in Example 1 was distilled by thin-film evaporation. Other than the fact that the distillation temperature was set to 145° C. and the evaporator inside pressure was set to 0.10 mmHg, the distillation was conducted in the same manner using the same thin-film evaporator as Example 1. The obtained distillate showed 98.5% of isosorbide purity, pH 4.75, yellow color and 92.0% of distillation yield, and the distillation time was 4 hours or less.

Example 5

The resulting liquid of conversion obtained after the neutralization and moisture removal in Example 1 was distilled by thin-film evaporation. Other than the fact that the distillation temperature was set to 170° C., the evaporator inside pressure was set to 1.40 mmHg and the vacuum pump was not connected to the branch line for vacuum formation, the distillation was conducted in the same manner using the same thin-film evaporator as Example 1. The obtained distillate showed 97.6% of isosorbide purity, pH 3.70, yellow color and 87.0% of distillation yield, and the distillation time was 4 hours or less.

Comparative Example 1

The resulting liquid of conversion obtained after the neutralization and moisture removal in Example 1 was distilled by thin-film evaporation. An external condenser type, thin-film evaporator was used. There was no additional depressurization through the output line for distillation residue. The distillation temperature was 180° C., and the evaporator inside pressure was about 3.0 mmHg. The obtained distillate showed 96.6% of isosorbide purity, pH 3.50, yellow color and 78.0% of distillation yield, and the distillation time was 4 hours or less.

Comparative Example 2

The resulting liquid of conversion obtained after the neutralization and moisture removal in Example 1 was distilled by thin-film evaporation. Other than the fact that the distillation temperature was set to 170° C. and the evaporator inside pressure was set to about 2.0 mmHg, the distillation was conducted in the same manner using the same external condenser type, thin-film evaporator as Comparative Example 1. The obtained distillate showed 97.2% of isosorbide purity, pH 3.70, yellow color and 80.2% of distillation yield, and the distillation time was 4 hours or less.

TABLE 1

Isosorbide purity, distillate pH, and distillation yield according to distillation condition

| | Distillation condition (temperature, pressure) | Purity (%) | Distillate pH | Distillation yield (%) |
|---|---|---|---|---|
| Example 1 | 170° C., 0.70 mmHg | 97.5 | 3.70 | 92.0 |
| Example 2 | 160° C., 0.45 mmHg | 98.5 | 4.00 | 92.0 |
| Example 3 | 150° C., 0.14 mmHg | 98.5 | 4.50 | 91.6 |
| Example 4 | 145° C., 0.10 mmHg | 98.5 | 4.75 | 92.0 |
| Example 5 | 170° C., 1.4 mmHg | 97.6 | 3.70 | 87.0 |
| Comparative Example 1 | 180° C., 3.0 mmHg | 96.6 | 3.50 | 78.0 |
| Comparative Example 2 | 170° C., 2.0 mmHg | 97.2 | 3.70 | 80.2 |

EXPLANATION OF THE SYMBOLS

1: Thin-film evaporator
2: Heating jacket
3: Wiper
4: Condenser guard
5: Internal condenser
6: Input line for raw material
7: Output line for distillation residue
7-1: Branch line for vacuum formation
8: Vacuum line
9: Output line for distillate
10: Cooler input line
11: Cooler output line

The invention claimed is:

1. A method for producing anhydrosugar alcohol comprising the steps of:
converting hydrogenated sugar to anhydrosugar alcohol by dehydration reaction, and distilling the resulting liquid of the converting step,
wherein the distilling step is conducted in an internal condenser type, thin-film evaporator comprising an internal condenser, an input line for raw material, an output line for distillation residue, a vacuum line and an output line for distillate.

2. The method for producing anhydrosugar alcohol according to claim 1, wherein when the distilling step is conducted, the inside of the evaporator is depressurized by pressure reduction through the vacuum line and additionally through the output line for distillation residue.

3. The method for producing anhydrosugar alcohol according to claim 1, wherein the hydrogenated sugar is hexitol and the anhydrosugar alcohol is dianhydrohexitol.

4. The method for producing anhydrosugar alcohol according to claim 1, wherein an acid catalyst is used in the step of converting hydrogenated sugar to anhydrosugar alcohol by dehydration reaction.

5. The method for producing anhydrosugar alcohol according to claim 1, wherein the resulting liquid of the step of converting hydrogenated sugar to anhydrosugar alcohol is pre-treated to remove moisture and low-boiling-point substance before being fed to the distilling step.

6. The method for producing anhydrosugar alcohol according to claim 1, wherein the distilling step is conducted under a temperature condition of from 100° C. to 170° C.

7. The method for producing anhydrosugar alcohol according to claim 1, wherein the distilling step is conducted under a pressure condition of 1 mmHg or less.

8. The method for producing anhydrosugar alcohol according to claim 1, wherein when the distilling step is conducted, the degree of vacuum of the vacuum line is the same as the degree of vacuum of the output line for distillation residue.

9. The method for producing anhydrosugar alcohol according to claim 1, wherein the distillate after the distilling step has an anhydrosugar alcohol purity of 97.5% or higher, a pH of 3.7 or higher, and a distillation yield of 87% or higher.

10. The method for producing anhydrosugar alcohol according to claim 1, wherein after the distilling step, a step of post-treatment is further conducted for the anhydrosugar alcohol resulting from the distillation, and wherein the post-treatment is selected from adsorbent treatment, ion purification, and a combination thereof.

11. A method for distilling liquid material by using an internal condenser type, thin-film evaporator comprising an internal condenser, an input line for raw material, an output line for distillation residue, a vacuum line and an output line for distillate, wherein when the distillation is conducted, the inside of the evaporator is depressurized by pressure reduction through the vacuum line and additionally through the output line for distillation residue.

* * * * *